ically as substituted 2-[(methylsulfinyl)acetyl]-3-heterocyclicindoles, various derivatives thereof, and to the processes for making and using such compositions as immunosuppressants.

United States Patent [19]
Steinman et al.

[11] 4,342,769
[45] Aug. 3, 1982

[54] 2-[(METHYLSULFINYL)ACETYL]-3-HETEROCYCLICINDOLES AND DERIVATIVES THEREOF AS IMMUNOSUPPRESSANTS

[75] Inventors: Martin Steinman, Livingston; Pirouz Tahbaz, Cedar Grove, both of N.J.

[73] Assignee: Schering Corporation, Kenilworth, N.J.

[21] Appl. No.: 143,700

[22] Filed: Apr. 25, 1980

Related U.S. Application Data

[62] Division of Ser. No. 947,979, Oct. 2, 1978, Pat. No. 4,225,711.

[51] Int. Cl.$^3$ .................. A61K 31/50; C07D 403/04
[52] U.S. Cl. .......................... 424/251; 260/326.12 R; 260/326.15; 424/263; 424/270; 424/272; 424/273 R; 424/273 P; 424/274; 544/238; 544/333; 544/405; 546/273; 548/181; 548/214; 548/215; 548/240; 548/336; 548/374; 549/59
[58] Field of Search .............. 424/250, 251, 270, 272, 424/273 R, 273 P, 274

[56]           References Cited
          U.S. PATENT DOCUMENTS 3,491,114  1/1970  Suh ........................................ 544/405
3,658,827  4/1972  Bezou .................................... 544/405
3,927,023 12/1975  Brown et al. ......................... 544/333
4,059,583 11/1977  McComsey et al. ................. 544/333
4,242,347 12/1980  Huebner ............................... 424/267

OTHER PUBLICATIONS

Adams, "J. Amer. Chem. Soc.", vol. 76, 1954, p. 3168.
Inaba, et al., "Chem. Pharm. Bull.", vol. 20, 1972, p. 1628.
Suthers, et al., "J. Org. Chem.", vol. 27, 1962, p. 447.
Bullock, et al., "J. Amer. Chem. Soc.", vol. 78, 1956, p. 5854.
Jerne, et al., "Cell-bound Antibodies", 1963, Wistar Institute Press, British J. Pharmacology, vol. 21, pp. 127–136 and vol. 24, pp. 632–640.
"Transplantation of Cells and Tissues", 1961, Wistar Institute Press, Uhr, Physiology Review, vol. 46, pp. 359–411.

Primary Examiner—Donald G. Daus
Assistant Examiner—James H. Turnipseed
Attorney, Agent, or Firm—Paul H. Ginsburg; Bruce M. Eisen

[57]                  ABSTRACT

This invention relates to compositions of matter classified in the art of chemistry as substituted 2-[(methylsulfinyl)acetyl]-3-heterocyclicindoles, various derivatives thereof, and to the processes for making and using such compositions as immunosuppressants.

24 Claims, No Drawings

2-[(METHYLSULFINYL)ACETYL]-3-HETEROCYCLICINDOLES AND DERIVATIVES THEREOF AS IMMUNOSUPPRESSANTS

This is a division of application Ser. No. 947,979, filed Oct. 2, 1978, now U.S. Pat. No. 4,225,711, issued Sept. 30, 1980.

The invention sought to be patented in one of its composition aspects resides in the chemical compounds 2-R-substituted-3-heterocyclicindoles wherein R is representative of such groups as methylsulfinylacetyl, methylsulfonylacetyl, methylthiohydroxyacetyl, methylthioalkoxyacetyl, methylsulfinylhydroxyethyl, methylsulfonylhydroxyethyl and the 3-position heterocycle is selected from the group consisting of pyridyl, pyrimidinyl, pyridazinyl, pyrazinyl, pyrazolyl, imidazolyl, thiazolyl, pyrrolyl, isothiazolyl, thienyl, furanyl, oxazolyl and isoxazolyl.

The invention sought to be patented in another of its composition of matter aspects resides in the concept of pharmaceutical dosage forms containing a herein defined substituted 3-pyridinylindole in admixture with a pharmaceutical carrier suitable for an enteral or parenteral administration.

The invention sought to be patented in one of its process aspects resides in the concept of administering to a mammal suffering from rheumatoid arthritis a therapeutically effective quantity of a substituted 2-R-3-heterocyclicindole wherein R is representative of such groups as methylsulfinylacetyl, methylsulfonylacetyl, methylthiohydroxyacetyl, methylthioalkoxyacetyl, methylsulfinylhydroxyethyl, methylsulfonylhydroxyethyl, and the 3-position heterocycle is selected from the group consisting of pyridyl, pyrimidinyl, pyridazinyl, pyrazinyl, pyrazolyl, imidazolyl, thiazolyl, isothiazolyl, thienyl, furanyl, pyrrolyl, oxazolyl and isoxazolyl.

More specifically, the tangible embodiments of this invention relate to those substituted 3-pyridylindoles having the structural formula:

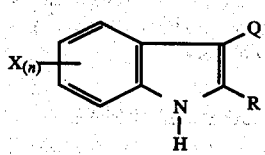

I wherein X is halogeno, (n) is an integer of zero to three, R is methylsulfinylacetyl, methylsulfonylacetyl, methylthiohydroxyacetyl, methylthioalkoxyacetyl, methylsulfinylhydroxylethyl or methylsulfonylhydroxyethyl and Q is selected from the group consisting of pyridyl, pyrimidinyl, pyridazinyl, pyridazinyl, pyrazinyl, pyrazolyl, imidazolyl, thiazolyl, isothiazolyl, thienyl, furanyl, pyrrolyl, oxazolyl and isoxazolyl.

The term "halogeno" includes chloro, bromo, fluoro and iodo. When the benzenoid moiety bears halogeno substituents, it is preferred that such substituent(s) be located in the 5- and/or 6-positions. Embraced within the definition of pyridyl are the 2-, 3- and 4-position pyridyl moieties, and the lower alkyl, particularly methyl, substituted pyridyl moieties. Similarly, in the case of the other 3-position heterocycles, all of the various position isomers by which such heterocyclics may be attached to the 3-position of the indole nucleus are contemplated. The methylsulfinylacetyl radical and derivatives thereof may be illustrated as follows:

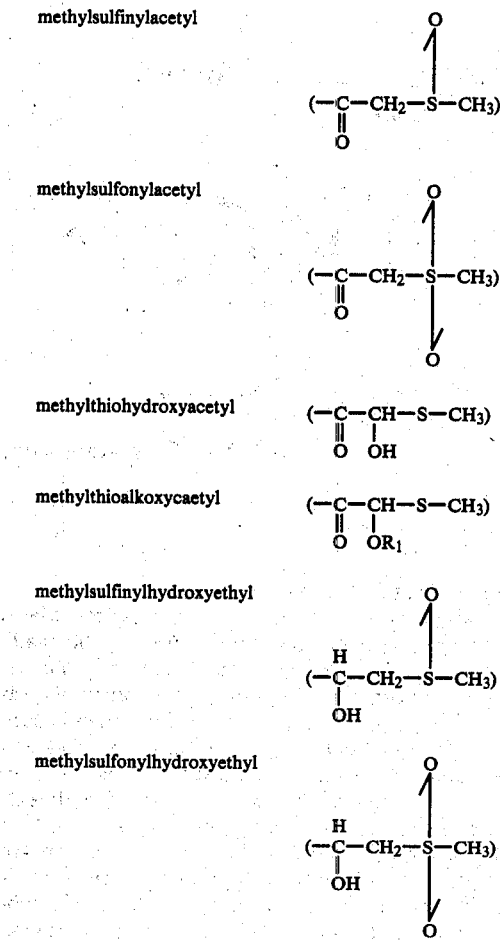

wherein $R_1$ is lower alkyl having up to six carbon atoms, preferably methyl.

In general, the compounds wherein R represents methylsulfinylacetyl may be prepared by reacting the appropriate alkyl X-substituted-3-Q-indole-2-carboxylates (III) with an anion of dimethylsulfoxide (II); the anion being a freshly prepared reactant which is obtained by warming dimethylsulfoxide in an inert organic solvent under an atmosphere of nitrogen in the presence of a base. Preferably, the warming takes place for about two hours at 65°-75° C. in a suitable solvent such as benzene. A preferred base is sodium hydride, although other equivalently functioning bases well known in the art may also be used. In effecting the reaction of the dimethylsulfoxide anion and the alkyl 3-Q-indole-2-carboxylates (III), the reactants are stirred together in an inert solvent at room temperature until reaction is complete (generally about 1-2 hours). Preferably, the anion is present in excess molar quantities (about 3 times) relative to the amount of the 3-Q-indole-2-carboxylate reactant. Following completion, the reaction mixture is quenched with water, the solutions acidified and the desired product isolated by filtration and purified by crystallization. This reaction may be schematically represented as follows:

Reaction Scheme A:

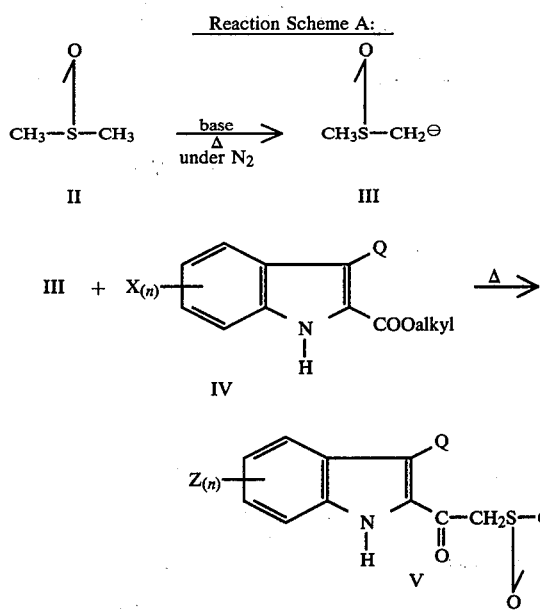

wherein X, Q and (n) are as previously defined.

The alkyl X-substituted-3-Q-indole-2-carboxylates (IV) are either known compounds or may be made according to techniques analogously known in the art. In essence, appropriately $X_{(n)}$ substituted phenylhydrazine acid halides are reacted with an appropriately substituted alkali metal salt of a β-Q-substituted pyruvate to produce an X-Q-substituted hydrazone, which is ring cyclized to produce the desired alkyl X-3-Q-indole-2-carboxylate. Often times this reaction will produce isomeric materials and in such instances, the isomers are preferentially separated by chromatographic techniques. For example, the cyclization of 3,4-dihalo substituted phenylhydrazone of an alkyl 2-pyridylpyruvate hydrochloride (by heating with glacial acetic acid) will provide a mixture containing an alkyl 5,6-dihalo-3-pyridylimdole-2-carboxylate and an alkyl 4,5-dihalo-3-pyridylindole-2-carboxylate. The mixture is chromatographed on silica gel, utilizing chloroform and the isomeric materials are easily separated. Of course, other standard techniques for the separation of isomers may also be utilized.

The required intermediates may be prepared by techniques well known to those of ordinary skill in the art. For example, ethyl 2-pyridylpyruvate-1-oxide is prepared according to Adams, et al (J. Amer. Chem. Soc. 76, 3168 (1954); the succeeding ethyl 2-pyridylpyruvate according to S. Inaba, et al (Chem. Pharm. Bull. 20, 1628 (1972)); the aniline reactants according to Suthers, et al (J. Org. Chem., 27, 447 (1962)); and the phenylhydrazines according to Bullock, et al (J. Amer. Chem. Soc., 78, 5854 (1956).

The remaining compounds of this invention are derivatives of the foregoing 2-(methylsulfinyl)acetyl-3-Q-indoles (V) and are prepared by techniques analogously known in the art. For example, by oxidizing the 2-(methylsulfinyl)acetyl-3-Q-indoles (V) with meta chloroperbenzoic acid there is formed the corresponding 2-(methylsulfonyl)acetyl-3-Q-indoles (VI). Subjecting the X-substituted-2-(methylsulfonyl)acetyl-3-Q-indoles to the Pummerer acid rearrangement will yield, depending upon the solvent, either the corresponding 2-(methylthiohydroxyl)acetyl-3-Q-indoles (VII) or the corresponding 2-(methylthioalkoxy)acetyl-3-Q-indoles (VIII). When the Pummerer reaction is effected in water, then the 2-(methylthiohydroxyl)acetyl-3-Q-indoles are obtained but when it is effected in an alkanol then the 2-(methylthioalkoxyl)acetyl-3-Q-indoles are prepared. These reactions may be depicted as follows:

Reaction Scheme B:

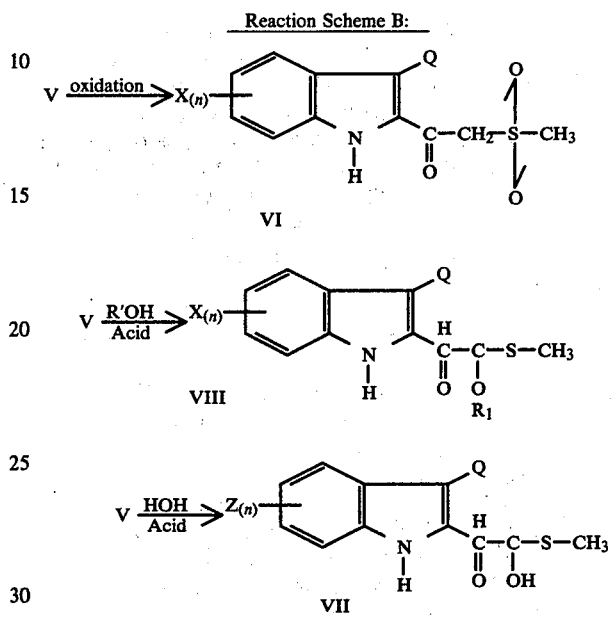

wherein X, O and (n) are as previously defined and $R^1$ is lower alkyl.

Alternatively, the 2-methylsulfinylacetyl (V) and the 2-methylsulfonylacetyl (VI) compounds may each be subjected to a selective chemical reduction with sodium borohydride wherein the carbonyl moiety of the 2-position substituent is preferentially reduced, i.e., neither the sulfinyl nor the sulfonyl moieties are reduced. By the selective chemical reduction the corresponding 2-methylsulfinylhydroxyethyl-3-Q-indole (IX) and the 2-methylsulfonylhydroxyethyl-3-Q-indole (X), respectively, are produced. This reaction may be schematically depicted as follows:

Reaction Scheme C:

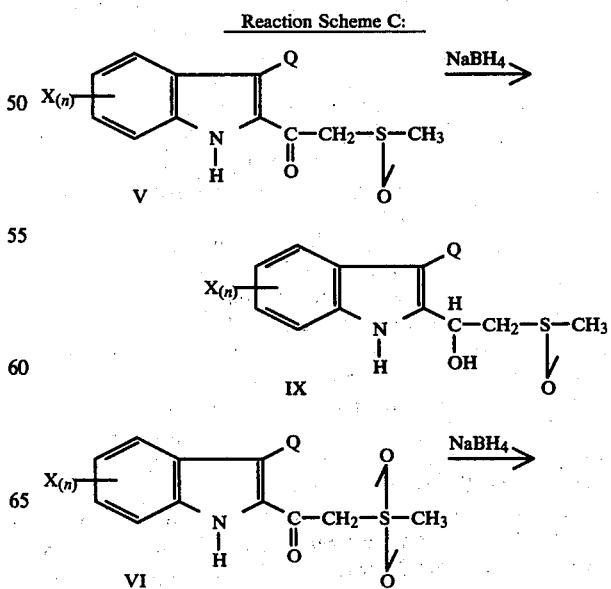

-continued
Reaction Scheme C:

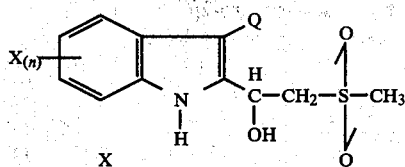

wherein X, Q and (n) are as previously defined.

Having described, in general terms, the procedures by which the compounds may be prepared, the following Examples illustrate the specific details by which, with the aid of analogy reasoning, teach those of ordinary skill in the art how to prepare the compounds embraced by this invention.

EXAMPLE I

6-BROMO-5-CHLORO-2[(METHYLSULFINYL)ACETYL]-3-(2-PYRIDYL)INDOLE

Step A

3-Bromo-4-chlorophenylhydrazine hydrochloride

3-Bromo-4-chloroaniline (41.3 g., 0.2 mole) in 90 ml of 6 N hydrochloric acid, cooled to −10° is treated with 14 g. of sodium nitrite in 30 ml. of water. Add this solution, with stirring, to a cold (−10° C.) solution of 55 g. of sodium bisulfite and 20 g. of sodium hydroxide in 200 ml. of water. After the red precipitate appears, allow the mixture to warm to room temperature. Add 200 ml. of concentrated hydrochloric acid and heat at 90°–100° C. for 4 hours. Allow the mixture to cool overnight, collect the material washing with 50 ml of cold 3 N hydrochloric acid. The product is dried. Recrystallization from ether-methanol yields the desired material, m.p. 208°–210° C.

Step B

3-Bromo-4-chlorophenylhydrazone of ethyl 2-pyridylpyruvate hydrochloride

Pass dry hydrochloric acid into 500 ml of dry ethanol containing 54.4 g of 3-bromo-4-chlorophenylhydrazine hydrochloride and 41.5 g of ethyl 2-pyridylpyruvate until 50 g. of the dry acid is absorbed. With constant stirring, reflux the resulting mixture for 2 hours, allow the mixture to cool overnight, collect and wash the precipitate with cold ethanol, and dry in vacuo to obtain the title compound, m.p. 207°–208° C.

Step C

Ethyl 6-bromo-5-chloro-3-(2-pyridyl)indole-2-carboxylate and Ethyl 4-bromo-5-chloro-3-(2-pyridyl)indole-2-carboxylate Add the 3-bromo-4-chlorophenylhydrazone of ethyl 2-pyridylpyruvate hydrochloride (86 g.) to 360 ml of glacial acetic acid with stirring and warm to 70° C. Add 80 ml of concentrated sulfuric acid dropwise over an hour maintaining a temperature of 80°–95° C. After a further 15 minutes, cool to 25° C. and pour onto ice. Adjust pH to 8–9 with ammonia. Collect the precipitate, wash with water and dry.

Treat the precipitate with 200 ml of methylene chloride, stirring for an hour. Filter, wash with methylene chloride and dry the insoluble material which is mainly the 6-bromo-5-chloro isomer. The filtrate contains both indoles.

The precipitate is crystallized from benzene to yield the 6-bromo-5-chloro isomer, m.p. 173°–175°. Recrystallization from benzene (charcoal) yields one spot material (thin layer chromatography); m.p. 179°–180°, analytical sample m.p. 181°–182°.

The methylene chloride filtrate is concentrated and cooled to yield light yellow crystals, m.p. 208°–210° of the 4-bromo-5-chloro isomer; analytical sample m.p. 209°–210°.

Step D

6-Bromo-5-chloro-2[(methylsulfinyl)acetyl]-3-(2-pyridyl)indole

Add 6.2 g of sodium hydride in mineral oil (50%) to 50 ml of DMSO at 15°–25°. Stir at ambient temperature for a further hour.

Cool to 15°, add 10 ml of water cautiously, and then add 190 ml more. Filter, and add 10 ml of acetic acid to the filtrate keeping the temperature below 20°. Decant to obtain the gray solid, stir with ether. Collect and wash with ether, dry to obtain the title compound, m.p. 198°–199° (dec.).

Similarly, by following the procedures set forth in the foregoing example, there are produced:
5-chloro-2[(methylsulfinyl)acetyl]-3-(2-pyridyl)indole,
4,5,6-trichloro-2[(methylsulfinyl)acetyl]-3-(2-pyridyl)indole,
5,6-dichloro-2[(methylsulfinyl)acetyl]-3-(2-pyridyl)indole,
4,5-dichloro-2[(methylsulfinyl)acetyl]-3-(2-pyridyl)indole,
6-chloro-2[(methylsulfinyl)acetyl]-3-(2-pyridyl)indole,
4,6-dibromo-2[(methylsulfinyl)acetyl]-3-(2-pyridyl)indole,
5-bromo-6-fluoro-2[(methylsulfinyl)acetyl]-3-(2-pyridyl)indole,
5,6-difluoro-2[(methylsulfinyl)acetyl]-3-(2-pyridyl)indole,
6-bromo-5-chloro-2[(methylsulfinyl)acetyl]-3-(3-pyridyl)indole,
6-bromo-5-chloro-2[(methylsulfinyl)acetyl]-3-(4-pyridyl)indole,
6-bromo-5-chloro-2[(methylsulfinyl)acetyl]-3-(2-oxazolyl)indole,
6-bromo-5-chloro-2[(methylsulfinyl)acetyl]-3-(3-isoxazolyl)indole,
6-bromo-5-chloro-2[(methylsulfinyl)acetyl]-3-(2-pyrimidinyl)indole,
6-bromo-5-chloro-2[(methylsulfinyl)acetyl]-3-(3-pyridazinyl)indole,
6-bromo-5-chloro-2[(methylsulfinyl)acetyl]-3-(2-pyrazinyl)indole,
6-bromo-5-chloro-2[(methylsulfinyl)acetyl]-3-(3-pyrazolyl)indole,
6-bromo-5-chloro-2[(methylsulfinyl)acetyl]-3-(2-imidazolyl)indole,
6-bromo-5-chloro-2[(methylsulfinyl)acetyl]-3-(2-thiazolyl)indole,
6-bromo-5-chloro-2[(methylsulfinyl)acetyl]-3-(3-isothiazolyl)indole,
6-bromo-5-chloro-2[(methylsulfinyl)acetyl]-3-(2-thienyl)indole,
6-bromo-5-chloro-2[(methylsulfinyl)acetyl]-3-(2-furanyl)indole and 6-bromo-5-chloro-2[(methylsulfinyl)acetyl]-3-(2-pyrrolyl)indole.

EXAMPLE 2

6-Bromo-5-Chloro-2[(methylsulfonyl)acetyl]-3-(2-pyridyl)indole

Stir a mixture of 6.0 g of 6-bromo-5-chloro-2[methylsulfinyl)acetyl]-3-(2-pyridyl)indole and 6.0 g of m-chloroperbenzoic acid in 150 ml of chloroform at room temperature for 2 hours. Concentrate the mixture to about 60 ml in vacuo, and filter and wash the product with 20 ml of cold chloroform to obtain 6-bromo-5-chloro-2[(methylsulfonyl)acetyl]-3-(2-pyridyl)indole.

By substituting the 6-bromo-5-chloro-2[(methylsulfinyl)acetyl]-3-(2-pyridyl)indole with the products obtained by the techniques of Example 1 and by substantially following the techniques of this example, there is produced the following compounds:
5-chloro-2](methylsulfonyl)acetyl]-3-(2-pyridyl)indole.
4,5,6-trichloro-2[(methylsulfonyl)acetyl]-3-(2-pyridyl)indole,
5,6-dichloro-2[(methylsulfonyl)acetyl]-3-(2-pyridyl)indole,
4,5-dichloro-2[(methylsulfonyl)acetyl]-3-(2-pyridyl)indole,
6-chloro-2[(methylsulfonyl)acetyl]-3-(2-pyridyl)indole,
4,6-dibromo-2[(methylsulfonyl)acetyl]-3-(2-pyridyl)indole,
5-bromo-6-fluoro-2[(methylsulfonyl)acetyl]-3-(2-pyridyl)indole,
5,6-difluoro-2[(methylsulfonyl)acetyl]-3-(2-pyridyl)indole,
6-bromo-5-chloro-2[(methylsulfonyl)acetyl]-3-(3-pyridyl)indole,
6-bromo-5-chloro-2[(methylsulfonyl)acetyl]-3-(4-pyridyl)indole,
6-bromo-5-chloro-2[(methylsulfonyl)acetyl]-3-(2-oxazolyl)indole,
6-bromo-5-chloro-2[(methylsulfonyl)acetyl]-3-(3-isooxazolyl)indole,
6-bromo-5-chloro-2[(methylsulfonyl)acetyl]-3-(2-pyrimidinyl)indole,
6-bromo-5-chloro-2[(methylsulfonyl)acetyl]-3-(3-pyridazinyl)indole,
6-bromo-5-chloro-2[(methylsulfonyl)acetyl]-3-(2-pyrazinyl)indole,
6-bromo-5-chloro-2[(methylsulfonyl)acetyl]-3-(3-pyrazolyl)indole,
6-bromo-5-chloro-2[(methylsulfonyl)acetyl]-3-(2-imidazolyl)indole,
6-bromo-5-chloro-2[(methylsulfonyl)acetyl]-3-(2-thiazolyl)indole,
6-bromo-5-chloro-2[(methylsulfonyl)acetyl]-3-(3-isothiazolyl)indole,
6-bromo-5-chloro-2[(methylsulfonyl)acetyl]-3-(2-thienyl)indole,
6-bromo-5-chloro-2[(methylsulfonyl)acetyl]-3-(2-furanyl)indole and
6-bromo-5-chloro-2[(methylsulfonyl)acetyl]-3-(2-pyrrolyl)indole.

EXAMPLE 3

6-Bromo-5-chloro-2[(1-hydroxy-2-methylsulfinyl)ethyl]-3-(2-pyridyl indole

To 6-bromo-5-chloro-2[(methylsulfinyl)acetyl]-3-(2-pyridyl)indole (2.5 g) in 50 ml of ethanol add 0.3 g of sodium borohydride and after a solution is obtained (about 10 minutes), stir the mixture for another 30 minutes. Slowly add 1 ml of acetic acid and then add 100 ml of water. Decant the liquid from the insoluble material, dissolve it in ethanol and add etherhexane to obtain 6-bromo-5-chloro-2[(1-hydroxy-2-methylsulfinyl)ethyl]-3-(2-pyridyl)indole.

By substituting the 6-bromo-5-chloro-2[(methylsulfinyl)acetyl]-3-(2-pyridyl)indole reactant of this example with those produces derived from Example 1 and by substantially following the techniques of this example there is produced the following compounds:
5-chloro-2[(1-hydroxy-2-methylsulfinyl)acetyl]-3-(2-pyridinyl)indole,
4,5,6-trichloro-2[(1-hydroxy-2-methylsulfinyl)acetyl]-3-(2-pyridyl)indole,
5,6-dichloro-2[(1-hydroxy-2-methylsulfinyl)acetyl]-3-(2-pyridyl)indole,
4,5-dichloro-2[(1-hydroxy-2-methylsulfinyl)acetyl]-3-(2-pyridyl)indole,
6-chloro-2[(1-hydroxy-2-methylsulfinyl)acetyl]-3-(2-pyridyl)indole,
4,6-dibromo-2[(1-hydroxy-2-methylsulfinyl)acetyl]-3-(2-pyridyl)indole,
5-bromo-6-fluoro-2[(1-hydroxy-2-methylsulfinyl)acetyl]-3-(2-pyridyl)indole,
5,6-difluoro-2[(1-hydroxy-2-methylsulfinyl)acetyl]-3-(2-pyridyl)indole
6-bromo-5-chloro-2[(1-hydroxy-2-methylsulfinyl)acetyl]-3-(2-pyridyl)indole,
6-bromo-5-chloro-2[(1-hydroxy-2-methylsulfinyl)acetyl]-3-(4-pyridyl)indole,
6-bromo-5-chloro-2[(1-hydroxy-2-methylsulfinyl)acetyl]-3-(2-oxazolyl)indole,
6-bromo-5-chloro-2[(1-hydroxy-2-methylsulfinyl)acetyl]-3-(3-isoxazolyl)indole,
6-bromo-5-chloro-2[(1-hydroxy-2-methylsulfinyl)acetyl]-3-(2-pyrimidinyl)indole,
6-bromo-5-chloro-2[(1-hydroxy-2-methylsulfinyl)acetyl]-3-(3-pyridazinyl)indole,
6-bromo-5-chloro-2[(1-hydroxy-2-methylsulfinyl)acetyl]-3-(2-pyrazinyl)indole,
6-bromo-5-chloro-2[(1-hydroxy-2-methylsulfinyl)acetyl]-3-(3-pyrazoly)indole,
6-bromo-5-chloro-2[(1-hydroxy-2-methylsulfinyl)acetyl]-3-(2-imidazol)indole,
6-bromo-5-chloro-2[(1-hydroxy-2-methylsulfinyl)acetyl]-3-(2-thiazoly)indole,
6-bromo-5-chloro-2[(1-hydroxy-2-methylsulfinyl)acetyl]-3-(3-isothiazolyl)indole,
6-bromo-5-chloro-2[(1-hydroxy-2-methylsulfinyl)acetyl]-3-(2-thienyl)indole,
6-bromo-5-chloro-2[(1-hydroxy-2-methylsulfinyl)acetyl]-3-(2-furanyl)indole, and
6-bromo-5-chloro-2[(1-hydroxy-2-methylsulfinyl)acetyl]-3-(2-pyrrolyl)indole.

EXAMPLE 4

6-Bromo-5-chloro-2[(1-hydroxy-2-methylsulfonyl)ethyl]-3-(2-pyridyl)indole

To 6-bromo-5-chloro-2[(methylsulfonyl)acetyl]-3-(2-pyridyl)indole (2.2 g) in 75 ml of ethanol add 0.175 g of sodium borohydride. After a solution is obtained (about 10 minutes) stir the mixture of another 30 minutes, then slowly add 2 ml of acetic acid. Treat with charcoal, filter and add 100 ml of water to the filtrate to obtain 6-bromo-5-chloro-2[1-hydroxy-2-methylsulfonyl)ethyl]-3-(2-pyridyl)indole.

Similarly, by substituting the 6-bromo-5-chloro-2[(methylsulfonyl)acetyl]-3-(2-pyridyl)indole reactant of this example with the compounds derived from the process of Example 3 and by substantially following the techniques of this example there is produced the following compounds:

5-chloro-2[(1-hydroxy-2-methylsulfonyl)acetyl]-3-(2-pyridyl)indole,
4,5,6-trichloro-2[(1-hydroxy-2-methylsulfonyl)acetyl]-3-(2-pyridyl)indole,
5,6-dichloro-2[(1-hydroxy-2-methylsulfonyl)acetyl]-3-(2-pyridyl)indole,
4,5-dichloro-2[(1-hydroxy-2-methylsulfonyl)acetyl]-3-(2-pyridyl)indole,
6-chloro-2[(1-hydroxy-2-methylsulfonyl)acetyl]-3-(2-pyridyl)indole,
4,6-bromo-2[(1-hydroxy-2-methylsulfonyl)acetyl]-3-(2-pyridyl)indole,
5-bromo-6-fluoro-2[(1-hydroxy-2-methylsulfonyl)acetyl]-3-(2-pyridyl)indole,
5,6-difluoro-2[(1-hydroxy-2-methylsulfonyl)acetyl]-3-(2-pyridyl)indole,
6-bromo-5-chloro-2[(1-hydroxy-2-methylsulfonyl)acetyl]-3-(3-pyridyl)indole,
6-bromo-5-chloro-2[(1-hydroxy-2-methylsulfonyl)acetyl]-3-(4-pyridyl)indole,
6-bromo-5-chloro-2[(1-hydroxy-2-methylsulfonyl)acetyl]-3-(2-oxazolyl)indole,
6-bromo-5-chloro-2[(1-hydroxy-2-methylsulfonyl)acetyl]-3-(3-isoxazolyl)indole,
6-bromo-5-chloro-2[(1-hydroxy-2-methylsulfonyl)acetyl]-3-(2-pyrimidinyl)indole,
6-bromo-5-chloro-2[(1-hydroxy-2-methylsulfonyl)acetyl]-3-(3-pyridazinyl)indole,
6-bromo-5-chloro-2[(1-hydroxy-2-methylsulfonyl)acetyl]-3-(2-pyrazinyl)indole,
6-bromo-5-chloro-2[(1-hydroxy-2-methylsulfonyl)acetyl]-3-(3-pyrazolyl)indole,
6-bromo-5-chloro-2[(1-hydroxy-2-methylsulfonyl)acetyl]-3-(2-imidazolyl)indole,
6-bromo-5-chloro-2[(1-hydroxy-2-methylsulfonyl)acetyl]-3-(2-thiazolyl)indole,
6-bromo-5-chloro-2[(1-hydroxy-2-methylsulfonyl)acetyl]-3-(3-isothiazolyl)indole,
6-bromo-5-chloro-2[(1-hydroxy-2-methylsulfonyl)acetyl]-3-(2-thienyl)indole,
6-bromo-5-chloro-2[(1-hydroxy-2-methylsulfonyl)acetyl]-3-(2-furanyl)indole, and
6-bromo-5-chloro-2[(1-hydroxy-2-methylsulfonyl)acetyl]-3-(2-pyrrolyl)indole,

EXAMPLE 5

6-Bromo-5-chloro-3-(2-pyridyl)indole-2-glyoxal methyl hemimercaptal

Slowly add 15 ml of 6 N hydrochloric acid to 6-bromo-5-chloro-2-[(methylsulfinyl)acetyl]-3-(2-pyridyl)indole (2 g) in dimethylsulfoxide (75 ml), stir the resulting mixture for 3 hours, quench with ice water, collect and dry the solid to yield 6-bromo-5-chloro-3-(2-pyridyl)indole-2-glyoxal methyl hemimercaptal.

By substituting the 6-bromo-5-chloro-2[(methylsulfinyl)acetyl]-3-(2-pyridyl)indole with the products obtained by the techniques of Example 1, and by substantially following the techniques of this example, there is produced the following compounds:

5-chloro-3-(2-pyridyl)indole-2-glyoxal methyl hemimercaptal,
4,5,6-trichloro-3-(2-pyridyl)indole-2-glyoxal methyl hemimercaptal,
5,6-dichloro-3-(2-pyridyl)indole-2-gloxal methyl hemimercaptal,
4,5-dichloro-3-(2-pyridyl)indole-2-gloxal methyl hemimercaptal,
6-chloro-3-(2-pyridyl)indole-2-glyoxal methyl hemimercaptal,
4,6-dibromo-3-(2-pyridyl)indole-2-glyoxal methyl hemimercaptal,
5-bromo-6-fluoro-3-(2-pyridyl)indole-2-glyoxal methyl hemimercaptal,
5,6-difluoro-3-(2-pyridyl)indole-2-glyoxal methyl hemimercaptal,
6-bromo-5-chloro-3-(3-pyridyl)indole-2-glyoxal methyl hemimercaptal,
6-bromo-5-chloro-3-(4-pyridyl)indole-2-glyoxal methyl hemimercaptal,
6-bromo-5-chloro-3-(oxazolyl)indole-2-glyoxal methyl hemimercaptal,
6-bromo-5-chloro-3-(isoxazolyl)indole-2-glyoxal methyl hemimercaptal,
6-bromo-5-chloro-3-(pyrimidinyl)indole-2-glyoxal methyl hemimercaptal,
6-bromo-5-chloro-3-(pyridazinyl)indole-2-glyoxal methyl hemimercaptal,
6-bromo-5-chloro-3-(pyrazinyl)indole-2-glyoxal methyl hemimercaptal,
6-bromo-5-chloro-3-(pyrazolyl)indole-2-glyoxal methyl hemimercaptal,
6-bromo-5-chloro-3-(imidazolyl)indole-2-glyoxal methyl hemimercaptal,
6-bromo-5-chloro-3-(thiazolyl)indole-2-glyoxal methyl hemimercaptal,
6-bromo-5-chloro-3-(thienyl)indole-2-glyoxal methyl hemimercaptal,
6-bromo-5-chloro-3-(furanyl)indole-2-glyoxal methyl hemimercaptal,
and 6-bromo-5-chloro-3-(pyrrolyl)indole-2-glyoxal methyl hemimercaptal.

EXAMPLE 6

6-Bromo-5-chloro-2[(methylthio)(methoxy)acetyl]-3-(2-pyridyl)indole

Add 2 ml of concentrated hydrochloric acid to 6-bromo-5-chloro-2[(methylsulfinyl)acetyl]-3-(2-pyridyl)indole (5.0 g) in 50 ml of methanol and 50 ml of tetrahydrofuran, warm the mixture to 60° for 2 hours. Cool, add water and the resulting solid is collected and dried to obtain 6-bromo-5-chloro-2[(methylthio) (methoxy)acetyl]-3-(2-pyridyl)indole.

Similarly, by following the procedures set forth in the foregoing example, there are produced:

5-chloro-2[(methylthio)(methoxy)acetyl]-3-(2-pyridyl)indole,
4,5,6-trichloro-2[(methylthio)(methoxy)acetyl]-3-(2-pyridyl)indole,
5,6-dichloro-2[(methylthio)(methoxy)acetyl]-3-(2-pyridyl)indole,
4,5-dichloro-2[(methylthio)(methoxy)acetyl]-3-(2-pyridyl)indole,
6-chloro-2[(methylthio)(methoxy)acetyl]-3-(2-pyridyl)indole,
4,6-dibromo-2[(methylthio(methoxy)acetyl]-3-(2-pyridyl)indole,
5-bromo-5-fluoro-2[(methylthio)(methoxy)acetyl]-3-(2-pyridyl)indole, 5,6-difluoro-2[(methylthio)(methoxy)acetyl]-3-(3-pyridyl)indole,
6-bromo-5-chloro-2[(methylthio)(methoxy)acetyl]-3-(3-pyridyl)indole,
6-bromo-5-chloro-2[(methylthio)(methoxy)acetyl]-3-(4-pyridyl)indole, 6-bromo-5-chloro-2[(methylthio)(methoxy)acetyl]-3-(2-oxazolyl)indole,
6-bromo-5-chloro-2[(methylthio)(methoxy)acetyl]-3-(3-isoxazolyl) indole,
6-bromo-5-chloro-2[(methylthio)(methoxy)acetyl]-3-(2-pyrimidinyl) indole,
6-bromo-5-chloro-2[(methylthio)(methoxy)acetyl]-3-(3-pyrazinyl)indole,
6-bromo-5-chloro-2[(methylthio)(methoxy)acetyl]-3-(2l-pyrazinyl-)-indole,
6-bromo-5-chloro-2[(methylthio)(methoxy)acetyl]-3-(3-pyrazolyl)indole,
6-bromo-5-chloro-2[(methylthio)(methoxy)acetyl]-3-(2-imidazolyl) indole,
6-bromo-5-chloro-2[(methylthio(methoxy)acetyl]-3-(2-thiazolyl)indole,
6-bromo-5-chloro-2[(methylthio)(methoxy)acetyl]-3-(3-isothiazolyl) indole,
6-bromo-5-chloro-2[(methylthio)(methoxy)acetyl]-3-(2-thienyl)indole,
6-bromo-5-chloro-2[(methylthio)(methoxy)acetyl]-3-(2-furanyl)indole,
and 6-bromo-5-chloro-2[(methylthio)(methoxy)acetyl]-3-(2-pyrrolyl) indole.

Similarly, by substituting the methanol of this example with equivalent quantities of straight and branched chain alcohols having up to six carbon atoms, the corresponding 2[(methylthio)(methoxy)acetyl]-3-(2-pyridyl-)indoles and other 3-position heterocyclic indoles are produced.

Also included within the scope of the foregoing examples, particularly Example 2, are the 4-oxazolyl, 5-oxazolyl, 4-isoxazolyl, 5-ixoxazolyl, 4-pyrimidinyl, 5-pyrimidinyl, 4-pyridazinyl, 5-pyridazinyl, 4-pyrazolyl, 4-imidazolyl, 4-thiazolyl, 5-thiazolyl, 4-isothiazolyl, 4-isothiazolyl, 3-thienyl, 3-furanyl and 3-pyrrolyl isomeric forms thereof.

The compounds of this invention have the applied use characteristic of inhibiting both antibody and cell-mediated immune reactions. The antibody immune reactions include the immune response to sheep erythrocytes and the immune response to trinitrophenylated liposaccharide in mice as assessed by the spleen assay of Jerne, et al., Cell-bound Antibodies, Wistar Institute Press, 1963. Immune reactions classified as cell-mediated, delayed type hypersensitivities include the late secondary migratory lesions in rats injected with Freund's adjuvant (in accordance with the techniques described in British J. Pharmacology, 21:127–136 and 24:632–640, skin transplant rejection in mice and rats and mammary gland rejection (as described in Transplantation of Cells and Tissues, Wistar Institute Press, 1961), contact and protein hypersensitivities in guinea pigs, rabbits and rats (Uhr, Physiology Review, 46:359–419) and experimental allergic encephalomyelitus in rats.

Immunosuppressive agents have found widespread clinical application within the last two decades for treating diseases in which there is direct or indirect evidence for an immune etiology. Although corticosteroids have been successfully used in the clinical management of autoimmune diseases and in suppression of rejection phenomena associated with organ transplantation, patients are rendered highly susceptible to infection by such treatment. Indeed, there is a higher incidence of mortality from infections among these patients than from the disease itself.

Azathioprine and cyclophosphamide are used alone or in conjunction with steroids in immunosuppressive therapy and, although they possess a steroid "sparing" effect, it has been very difficult to develope therapeutic regimens that yield clinical improvement in the absence of untoward side effects, most notably bone marrow depression. Also, both drugs have a slow onset of action so that therapeutically beneficial effects are apparent only after approximately three weeks of treatment.

From the aforementioned tests as well as comparison with known immunosuppressants, the compounds are effective in suppressing the immune response at about 0.5 to 50 mpk. Disease states for which the immunosuppressant activity of the compounds of this invention are useful include rheumatoid arthritis, ulcerative colitis, allergies, systemic lupus erythematosus, hemalytic anemia, Crohn's disease, and the like. In their use as immunosuppressants the compounds have low toxicity and are non-cytotoxic at therapeutic doses. In their use, the compounds of this invention may be combined with inert pharmaceutical excipients such as lactose, mannitol, starch and other such inert pharmaceutical carriers when formulated into such dosage forms as tablets, capsules suppositories, and the like. For parenteral usage, the compounds may be formulated with an inert, parenterally acceptable vehicle, such as water, saline, sesame oil and the like. These formulations may be compounded according to the techniques well known to those of ordinary skill in the pharmaceutical art. Preferably the compounds may be administered in 3–4 daily doses although the specific regimen will be dictated by the severity and nature of the particular disease states.

As is true in most large classes of chemical compounds useful in the treatment of diseases, certain subgeneric groups and certain specific compounds are more preferred than others. Insofar as the instant X,Y-substituted-2-R-3-Q-indoles (I) are concerned, those compounds wherein R represents methylsulfinylacetyl or methylsulfonylacetyl are most preferred. Further, it is found that compounds having a halogeno substituent at the 5- and/or 6-positions are preferred whilst substitution at the 3-position is most rewarding when Q is pyridyl, preferably 2-pyridyl. Most preferred specific compound is 6-bromo-5-chloro-2[(methylsulfinyl)acetyl]-3-(2-pyridyl)indole, whilst:
6-bromo-5-chloro-2[(methylsulfinyl)acetyl]-3-(3-pyridyl)indole,
6-bromo-5-chloro-2[(methylsulfinyl)acetyl]-3-(4-pyridyl)indole,
6-bromo-5-chloro-2[(methylsulfinyl)acetyl]-3-(oxazolyl)indole,
6-bromo-5-chloro-2[(methylsulfinyl)acetyl]-3-(isoxazolyl)indole,
6-bromo-5-chloro-2[(methylsulfinyl)acetyl]-3-(pyrimidinyl)indole,
6-bromo-5-chloro-2[(methylsulfinyl)acetyl]-3-(pyridazinyl)indole,
6-bromo-5-chloro-2[(methylsulfinyl)acetyl]-3-(pyrazinyl)indole,
6-bromo-5-chloro-2[(methylsulfinyl)acetyl]-3-(pyrazolyl)indole,
6-bromo-5-chloro-2[(methylsulfinyl)acetyl]-3-(imidazolyl)indole, 6-bromo-5-chloro-2[(methylsulfinyl)acetyl]-3-(thiazolyl)indole, 6-bromo-5-chloro-2[(methylsulfinyl)acetyl]-3-(isothiazolyl)indole, 6-bromo-5-chloro-2[(methylsulfinyl)acetyl]-3-(thienyl)indole, 6-bromo-5-chloro-2[(methylsulfinyl)acetyl]-3-(furanyl)indole, and 6-bromo-5-chloro-2[(methylsulfinyl)acetyl]-3-(pyrrolyl)indole are also preferred species.

What is claimed is:

1. An pharmaceutical composition therapeutically useful in immunosuppression and arthritis comprising a therapeutically effective amount of a compound of the formula

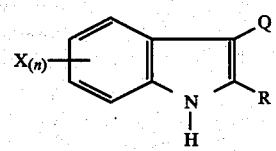

wherein X is halogeno, n is an integer of zero to three, R is methylsulfinylacetyl, methylsulfonylacetyl, methylthiohydroxyacetyl, methylthioalkoxyacetyl wherein the alkoxy group has one to six carbon atoms, methylsulfinylhydroxyethyl or methylsulfonylhydroxyethyl and Q is selected from the group consisting of pyridyl, oxazolyl, isoxazolyl, pyrimidinyl, pyridazinyl, pyrazinyl, pyrazolyl, imidazolyl, thiazolyl, isothiazolyl, thienyl, furanyl and pyrrolyl, together with a pharmaceutically acceptable carrier.

2. A composition of claim 1 wherein Q is pyridyl.
3. A composition of claim 1 wherein Q is 2-pyridyl.
4. A composition of claim 1 wherein n is two.
5. A composition of claim 1 wherein n is two and Q is oxazolyl.
6. A composition of claim 1 wherein n is two and Q is isoxazolyl.
7. A composition of claim 1 wherein n is two and Q is pyrimidinyl.
8. A composition of claim 1 wherein n is two and Q is pyridazinyl.
9. A composition of claim 1 wherein n is two and Q is pyrazinyl.
10. A composition of claim 1 wherein n is two and Q is pyrazolyl.
11. A composition of claim 1 wherein n is two and Q is imidazolyl.
12. A composition of claim 1 wherein n is two and Q is thiazolyl.
13. A composition of claim 1 wherein n is two and Q is isothiazolyl.
14. A composition of claim 1 wherein n is two and Q is thienyl.
15. A composition of claim 1 wherein n is two and Q is furanyl.
16. A composition of claim 1 wherein n is two and Q is pyrrolyl.
17. A composition of claim 1 wherein n is two and Q is pyridyl.
18. A composition of claim 1 wherein n is two and Q is 2-pyridyl.
19. A composition of claim 1 wherein n is two and R is methylsulfinylacetyl.
20. A composition of claim 1 wherein n is two, Q is pyridyl and R is methylsulfinylacetyl.
21. A composition of claim 1 wherein n is two, Q is 2-pyridyl and R is methylsulfinylacetyl.
22. A composition of claim 1, wherein said compound is 6-bromo-5-chloro-2[(methylsulfinyl)acetyl]-3-(2-pyridyl)indole.
23. A method for treating rheumatoid arthritis which comprises administering to a mammal suffering from rheumatoid arthritis a therapeutically effective quantity of a compound having the formula

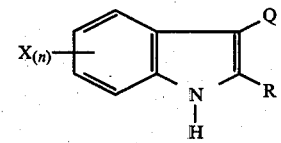

wherein X is halogeno, n is an integer of zero to three, R is methylsulfinylacetyl, methylsulfonylacetyl, methylthiohydroxyacetyl, methylthioalkoxyacetyl wherein the alkoxy group has one to six carbon atoms, methylsulfinylhydroxyethyl or methylsulfonylhydroxyethyl and Q is selected from the group consisting of pyridyl, oxazolyl, isoxazolyl, pyrimidinyl, pyridazinyl, pyrazinyl, pyrazolyl, imidazolyl, thiazolyl, isothiazolyl, thienyl, furanyl and pyrrolyl.

24. A method for eliciting an immunosuppressant response in a mammal suffering from a condition responsive to an immunosuppressant which comprises administering a therapeutically effective amount of a compound of the formula

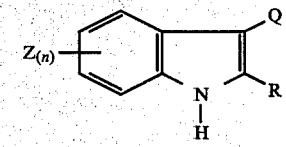

wherein X is halogeno, n is an integer of zero to three, R is methylsulfinylacetyl, methylsulfonylacetyl, methylthiohydroxyacetyl, methylthioalkoxyacetyl wherein the alkoxy group has one to six carbon atoms, methylsulfinylhydroxyethyl or methylsulfonylhydroxyethyl and Q is selected from the group consisting of pyridyl, oxazolyl, isoxazolyl, pyrimidinyl, pyridazinyl, pyrazinyl, pyrazolyl, imidazolyl, thiazolyl, isothiazolyl, thienyl, furanyl and pyrrolyl.

* * * * *